United States Patent [19]

Bridger

[11] 4,210,599

[45] Jul. 1, 1980

[54] SYNTHESIS OF BOROXAROPHENANTHRENES

[75] Inventor: Robert F. Bridger, Hopewell, N.J.

[73] Assignee: Mobil Oil Corporation, New York, N.Y.

[21] Appl. No.: 12,410

[22] Filed: Feb. 15, 1979

Related U.S. Application Data

[63] Continuation-in-part of Ser. No. 896,268, Apr. 14, 1978, abandoned.

[51] Int. Cl.$^2$ .............................................. C07F 5/04
[52] U.S. Cl. ................................................ 260/462 C
[58] Field of Search ......................... 260/462 C, 502.3

[56] References Cited

U.S. PATENT DOCUMENTS

| | | | |
|---|---|---|---|
| 3,203,928 | 8/1965 | Willcockson et al. | 260/462 C X |
| 3,287,270 | 11/1966 | McCabe et al. | 260/462 C X |
| 3,397,228 | 8/1968 | Brownstein | 260/462 C X |
| 3,417,123 | 12/1968 | Offenhauer | 260/462 C |
| 3,437,596 | 4/1969 | McCabe | 260/462 C X |

*Primary Examiner*—Helen M. S. Sneed
*Attorney, Agent, or Firm*—Charles A. Huggett; RaymondW. Barclay; Claude E. Setliff

[57] ABSTRACT

Improved synthesis of boroxarophenanthrenes, comprising the step of adding gaseous BCl$_3$ to a liquid hydrocarbon slurry of 2-hydroxybiphenyl at a specified temperature. Known methods involve the reaction of BCl$_3$ with the phenol at $-70°$ C., the reaction being carried out in methylene chloride.

16 Claims, No Drawings

SYNTHESIS OF BOROXAROPHENANTHRENES

CROSS REFERENCE TO RELATED APPLICATIONS

This application is a continuation-in-part of U.S. application Ser. No. 896,268, filed Apr. 14, 1978, and now abandoned.

BACKGROUND OF THE INVENTION

1. Field of the Invention

The invention relates to the synthesis of boroxarophenanthrenes. Specifically, it relates to the preparation of 10-hydroxy-10,9-boroxarophenanthrene by reaction of $BCl_3$ with o-phenylphenol in a liquid hydrocarbon slurry at from about 0° to about 80° C. room temperature.

The product is useful as an antioxidant (see U.S. Pat. Nos. 3,287,270 or 3,320,165) or as an antifatigue agent for lubricants.

2. Discussion of the Prior Art

It is well known that lubricating oil fractions are subject to deterioration from fatigue and oxidation under conditions of use such as in modern internal combustion engines. Oxidation products are formed in the oil which products are acidic in nature and exert an oxidative effect on metal parts with which the oil comes in contact. Furthermore, these oxidation products produce formations of varnish and sludge on the engine surfaces. This tends to lower the operating efficiency of the engine. The proper lubrication of engine parts is further hampered due to the detrimental effect of oxidation on the viscosity of the oil. Similarly, it is known that the oxidation of fuels, particularly during storage, causes gum formation and layer deposits which tend to cause operating malfunctions.

In order to overcome, insofar as possible, these undesirable effects, additives known as antioxidants are normally added to the lubricants and fuels. For example, phenolic or amine compounds are commonly employed as such additives. Modern technology, however, requires lubricants and fuels possessing increased resistance to oxidation.

It has been found that certain 10,9-boroxarophenanthrenes are effective in improving the oxidation and fatigue properties of lubricants. However, the presently known method of making them is time consuming and expensive. The known method is exemplified in U.S. Pat. No. 3,287,270.

Another reference of interest to this invention is U.S. Pat. No. 3,437,596 which, like U.S. Pat. No. 3,287,270, discloses the addition of a phenylphenol to a mixture of $BCl_3$ and methylene while maintaining the mixture at from −50° C. to −70° C.

SUMMARY OF THE INVENTION

The invention provides an improved process for synthesizing certain boroxarophenanthrenes by reacting $BCl_3$ with o-phenylphenol, warming and removing the chloride formed and the excess $BCl_3$ and solvent, heating the product thus formed in the presence of aluminum halide and treating with water, the improvement whereby the $BCl_3$ is added to a slurry of o-phenylphenol maintained at from about 0° C. to about 80° C., preferably at from about 20° C. to about 40° C.

These 10,9-boroxarophenanthrene compounds may be represented by the general formula:

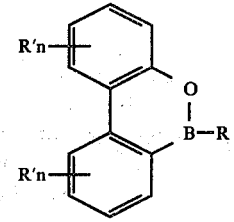

where R represents hydroxy, hydrocarbylamino, hydrocarbylthio, hydrocarbyl, oxy-hydrocarbyl, halogen, halogenated hydrocarbyl, halogenated oxy-hydrocarbyl groups or, in the case of the anhydride, an oxy-10,9-boroxarophenanthrene group, R' represents the same or different hydrocarbyl, halogen or halogenated hydrocarbyl groups or hydrogen, and n is an integer from 1 to 4, preferably 1 or 2.

As used herein, by the term "hydrocarbyl" is meant groups composed of carbon and hydrogen atoms such as aliphatic, aryl, aliphatic-aryl, both alkaryl and aralkyl, and cycloaliphatic groups, containing from 1 to 30 carbon atoms.

Suitable substituents for R include the abovementioned hydroxy group as well as alkyl groups, both straight-chain and branched-chain, such as methyl, ethyl, propyl, isopropyl, tert-butyl, octyl, dodecyl, hexadecyl, octadecyl, tetracosyl triacontyl and the like; aryl groups such as phenyl, naphthyl, and the like; aliphatic-aryl groups including tolyl, amylphenyl, phenyloctyl, and the like; cycloaliphatic groups such as cyclohexyl; oxy-hydrocarbyl groups such as any of the aforementioned hydrocarbyl groups attached to an oxygen atom, e.g., alkoxy, aryloxy groups, and the like; halogens such as chlorine, bromine, iodine; halognated hydrocarbyl and halogenated oxy-hydrocarbyl groups additionally containing one or more halogen atoms. The R' substituents may be selected from any of the hydrocarbyl, halogen, and halogenated hydrocarbyl groups hereinabove described as suitable for R.

Hydrocarbyl, oxy-hydrocarbyl, halogenated hydrocarbyl and halogenated oxy-hydrocarbyl groups containing from 1 to about 30, particularly from 1 to about 18 carbon atoms are preferred substituents.

Some examples of the 10,9-boroxarophenanthrene compounds used in accordance with the present invention are:

10-hydroxy-10,9-boroxarophenanthrene,
di-octadecyl-10-hydroxy-10,9-boroxarophenanthrene,
the anhydride of 10-hydroxy-10,9-boroxarophenanthrene,
10-tert-butoxy-10,9-boroxarophenanthrene,
10-methoxy-10,9-boroxarophenanthrene,
10-chloro-10,9-boroxarophenanthrene,
10-phenyl-10,9-boroxarophenanthrene,
the 1,17-trihydroperfluoro-heptyl ester of 10-hydroxy-10,9-boroxarophenanthrene,
the 2,2-difluoro-dodecyl ester of 10-hydroxy-10,9-boroxarophenanthrene,
1,3-dibromo-10-hydroxy-10,9-boroxarophenanthrene, and
1,3,7-tribromo-10-hydroxy-10,9-boroxarophenanthrene.

The 10,9-boroxarophenthrene compounds of the present invention possess surprisingly effective antioxidant properties, and indeed, they are superior in antioxidant properties to several widely used, commercial antioxidants.

While organo boron compounds have been employed heretofore as antioxidants, these prior art materials were of the borate-type. Such borates were hydrolytically unstable and exhibited only moderate antioxidant properties. The 10,9-boroxarophenanthrene compounds of this invention are not borates. For example, 10-hydroxy-10,9-boroxarophenanthrene, a preferred compound of this invention, may be described as internal ester of 2-(2-hydroxy phenol)-phenylboronic acid wherein the ring system containing the boron possesses an unusual degree of stability due to its aromaticity. The anhydride of 10-hydroxy-10,9-boroxarophenanthrene is hydrolytically stable.

DESCRIPTION OF SPECIFIC EMBODIMENTS

The boroxarophenanthrenes of this invention, as the art knows, possess surprisingly effective antioxidant properties, as well as antifatigue properties, when added to lubricants. Their preparation is well documented, as for example, in an article by Dewar and Dietz in J. Chem. Soc. (London), 1344 (1960) and in U.S. Pat. No. 3,287,270, which are incorporated herein by reference.

U.S. Pat. No. 3,287,270 discloses a series of steps necessary to the preparation of the compounds of the invention, as exemplified by 10-hydroxy-10,9-boroxarophenanthrene. Briefly, orthophenylphenol (1) is reacted with excess boron trichloride. The product (3) from this reaction is then heated in the presence of aluminum chloride to give 10-chloro-10,9-boroxarophenanthrene (4). This chloro compound is then treated with water to give the desired 10-hydroxy-10,9-boroxarophenanthrene (5). While the patent exemplifies the use of aluminum chloride, it is contemplated that aluminum halides in general will be useful also. These will particularly include aluminum bromide, but will also include the fluoride and iodide.

Although the present invention is not limited to any particular theory, it is believed that the above reactions may be represented as follows:

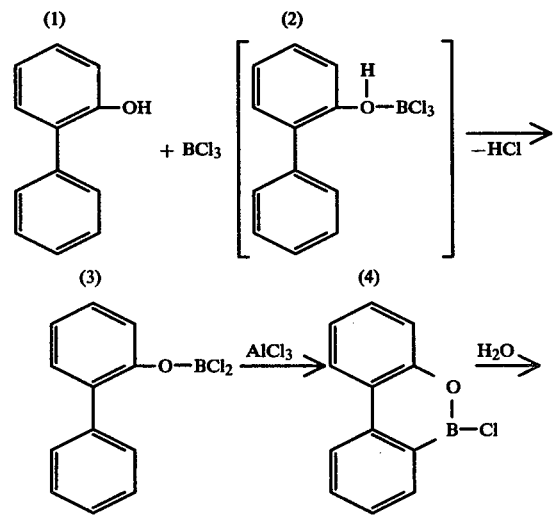

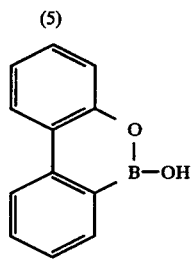

The process is an effective means for preparing the phenanthrenes, but it does have its disadvantages. These are solved by the present process.

To obtain those boroxarophenanthrenes wherein R is other than hydroxy, compound (4) may be reacted with an alcohol or phenol to yield the oxy-hydroxycarbyl group, with a hydrocarbylamine to give the hydrocarbyl-amino group, with a hydrocarbyl mercaptan to obtain the hydrocarbyl thio group or a grignard reagent to obtain the hydrocarbyl group. These will be selected so that the group attached to the boron atom will be the R group as defined above or will be an entity terminating in such R group, and the reactions to form such R groups will be carried out at from 5° C. to about 60° C. Equivalent amounts of these reactants and compound (4) are preferred, but an excess of such reactants to form the R group may be used.

In the prior art process, the addition of the boron trichloride to the phenylphenol must be carried out at −70° C. or lower, obviously requiring costly cooling equipment. The yields reported by Dewar and Dietz were of the order of 40% (although using their method, I have obtained yields of up to about 57%). Furthermore, in the prior art synthesis, phenol must be added very slowly to a $BCl_3$-methylene chloride solution so as to minimize formation of the diaryl chloroborate, thus wasting a mole of the phenylphenol upon cyclization.

I have found that these problems can be overcome merely by modifying the $BCl_3$-phenylphenol reaction step. In essence, gaseous boron trichloride is added to a liquid hydrocarbon slurry of the phenylphenol at the specified temperature. The preferred liquid hydrocarbons are those in which the phenylphenol has low solubility. These include naphtha, pentane, hexane, heptane and the like. Alkanes of moderate boiling points are especially preferred because the work-up after reaction is made easier.

Specifically, the phenylphenol may be slurried in hexane to the extent of from about 1 g. of phenol per 1 ml. of hexane to 1 g. of phenol to 100 ml. of hexane and the boron trichloride is sparged into the slurry at room temperature. From 1.0 to 2.0 moles, preferably 1.1 to 1.5 moles, of boron trichloride per mole of the phenylphenol are added at a rate that will enable the temperature to be at from about 0° to 80° C., preferably about 20° to 40° C. The preferred time of reaction will vary from about 15 minutes to about 1 hour. Optimum results, however, seem to be obtained the less the time of addition.

Except for this improved step, the remainder of the process remains much as it is in the art, as exemplified by U.S. Pat. No. 3,278,270.

Having described the invention generally, the following Examples will serve as specific illustrations. They are illustrations only, and it will be understood that the only limitations imposed on the scope of the invention will be found in the claims appended hereto.

EXAMPLE 1

The following description is of the synthesis of 10-hydroxy-10,9-boroxarophenanthrene by the prior method of Dewar and Dietz, referenced hereinabove.

Boron trichloride (117 g., 1 mol) was condensed into a 1 liter reaction flask containing methylene chloride (225 ml.) at −70° C. in 20 minutes. To this solution was added dropwise in 1 hour a solution of o-hydroxybiphenyl (127.5 g., 0.75 mol) in methylene chloride (200 ml.), keeping the temperature at −70° C. during the addition.

The solution was allowed to warm to room temperature overnight. The methylene chloride solvent was removed at reduced pressure (30°–35° C., 1 mm. Hg), and replaced with hexane (200 ml.). Anhydrous aluminum chloride (2 g.) was added, and the mixture was heated at reflux (55° to 60° C.) for 20 hours, filtered and stripped of solvent at reduced pressure. The oily residue was taken up in ether (500 ml.) and treated, with stirring, with 100 ml. water. After separation of excess water, the ether solution was dried and evaporated to give 83 g. (56% yield) of crude 10-hydroxy-10,9-boroxarophenanthrene of about 90% purity, melting 185°–190° C. Recrystallization from benzene gave 52.9 g. (36% yield) of white crystals melting at 214°–215° C.

EXAMPLE 2

The following example demonstrated the improvement in yield afforded by adding gaseous BCl3 to a hexane suspension of o-hydroxybiphenyl in the first step of the reaction.

Gaseous boron trichloride (59.0 g., 0.5 mol) was bubbled into a stirred slurry of 2-hydroxybiphenyl (63.8 g., 0.375 mol) suspended in hexane (250 ml.) in 23 minutes. During the addition, the temperature of the reaction mixture rose from 25° C. to 36° C. After addition of the BCl3 was complete, 1.0 g. of anhydrous aluminum chloride was added, and the mixture was refluxed for 6 hours. The mixture was cooled to room temperature and 200 ml. of ethyl ether and 50 ml. of water were added, and the mixture was stirred at room temperature for 30 minutes. After removal of excess water and drying, the solvent was filtered and then evaporated to give 62.5 g. (85% yield) of crude 10-hydroxy-10,9-boroxarophenanthrene, m.p. 188°–191° C., which was found by ultraviolet adsorption to be of 90% purity. Thin layer chromatography showed 2-hydroxy-biphenyl to be the only impurity. Upon recrystallization from benzene, 47 grams (64% yield) of white crystalline pure material were obtained, m.p. 214.5°–215° C. Dewar and Dietz, (op. cit.) reports m.p. of 205°–206.5° C.

EXAMPLE 3

The preparation described in Example 2 was repeated, except that the amount of boron trichloride was 70 g. (0.60 mol). The crude yield of 10-hydroxy-10,9-boroxarophenanthrene was 58.0 grams (79% yield) of material of 92% purity.

While Examples 1 and 2 report obtaining the pure product, this was only for characterization and was not otherwise necessary. In other words, the crude product is acceptable for use as a lubricant additive.

The base fluids for which the compounds of this invention find utility include gasoline, petroleum products of both lubricating and fuel viscosities, and synthetic fluids. Of the latter class may be included synthetic ester lubricants, such as those formed from monohydric alcohols and dicarboxylic acids, glycols or glycerols with monocarboxylic acids, and pentaerythritols with carboxylic acids, including alcohols having from about 4 to about 20 carbons, and carboxylic acids having from 2 to about 18 carbon atoms. Many synthetic esters may have mixed alcohols or carboxylic acids. Commonly may be included 2-ethylhexyl sebacate, trimethylolpropane trioctanoate, and especially pentaerythritol esters of valeric acid, isovaleric acid, caproic acid, caprylic acid, pelargonic acid, carpric acid, and the like. Of special interest is mixed pentaerythritol ester of an equimolar proportion of commercial valeric acid (containing isovaleric acid) and pelargonic acid. Other synthetic fluids include liquid polyolefins, alkylene oxide fluids, silicone fluids, polyacetals, and simple hydrocarbons of stable fluid viscosities.

I claim:

1. In an improved process for synthesizing a boroxarophenanthrene, which comprises the steps of reacting gaseous BCl3 with o-phenylphenol to form an intermediate product having the formula

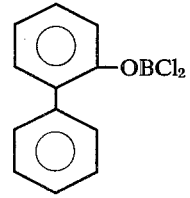

heating this intermediate in the presence of an aluminum halide and treating the product thus obtained with the appropriate reagent to obtain the said boroxarophenanthrene, the improvement whereby the BCl3 is added to a liquid hydrocarbon slurry of o-phenylphenol maintained at a temperature of from about 0° C. to about 80° C.

2. The process of claim 1 wherein the halide is chloride.

3. In an improved process for reacting gaseous BCl3 with o-phenylphenol to form a product having the formula

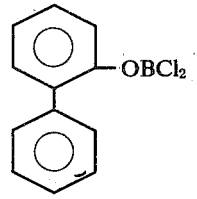

the improvement comprising the step of adding the BCl3 to a liquid hydrocarbon slurry of o-phenylphenol maintained at a temperature of from about 0° C. to about 80° C.

4. The process of claim 1 wherein said reagent is water.

5. The process of claim 4 wherein from about 1.0 to about 2.0 moles of BCl3 per mole of o-phenylphenol is used.

6. The process of claim 5 wherein from about 1.1 to about 1.5 moles of BCl3 per mole of o-phenylphenol is used.

7. The process of claim 1 where the time of reaction during the improvement ranges from about 15 minutes to about 1 hour.

8. The process of claim 1 wherein the liquid hydrocarbon is hexane.

9. The process of claim 1 wherein the temperature during said improvement is from about 20° to about 40° C.

10. An improved process for synthesizing a 10-hydroxy-10-9-boroxarophenanthrene by reacting gaseous $BCl_3$ with o-phenylphenol, warming, removing the hydrogen chloride formed, removing the excess $BCl_3$ and solvent, heating the product thus formed in the presence of aluminum halide and treating with water, the improvement whereby the $BCl_3$ is added to a liquid hydrocarbon slurry of o-phenylphenol maintained at a temperature of from about 0° to about 80° C.

11. The process of claim 10 wherein from about 1.0 to about 2.0 moles of $BCl_3$ per mole of o-phenylphenol is used.

12. The process of claim 11 wherein from about 1.1 to about 1.5 moles of $BCl_3$ per mole of o-phenylphenol is used.

13. The process of claim 10 wherein the time of reaction during the improvement ranges from about 15 minutes to about 1 hour.

14. The process of claim 10 wherein the liquid hydrocarbon is hexane.

15. The process of claim 10 wherein the temperature during said improvement is from about 20° to about 40° C.

16. The process of claim 10 wherein the halide is chloride.

* * * * *

Disclaimer 4,210,599.—*Robert F. Bridger,* Hopewell, N.J. SYNTHESIS OF BOROXAROPHENANTHRENES. Patent dated July 1, 1980. Disclaimer filed Aug. 13, 1981, by the assignee, *Mobil Oil Corp.*

Hereby enters this disclaimer to claims 1 through 16 of said patent.

[*Official Gazette December 15, 1981.*]